United States Patent
Morozova et al.

(10) Patent No.: US 9,999,614 B2
(45) Date of Patent: Jun. 19, 2018

(54) COMBINATION FOR THE PROPHYLAXIS AND TREATMENT OF BEHAVIOURAL, MENTAL, AND COGNITIVE DISORDERS

(71) Applicants: Margarita Alekseevna Morozova, Moscow (RU); Allan Gerovich Beniashvili, Moscow (RU); Maxim Eduardovich Zapolskii, Moscow (RU)

(72) Inventors: Margarita Alekseevna Morozova, Moscow (RU); Allan Gerovich Beniashvili, Moscow (RU); Maxim Eduardovich Zapolskii, Moscow (RU)

(73) Assignee: LTD "VALENTA-INTELLEKT", Moscow (RU)

( * ) Notice: Subject to any disclaimer, the term of this patent is extended or adjusted under 35 U.S.C. 154(b) by 0 days. days.

(21) Appl. No.: 14/432,225

(22) PCT Filed: Nov. 7, 2012

(86) PCT No.: PCT/RU2012/000906
§ 371 (c)(1),
(2) Date: Mar. 30, 2015

(87) PCT Pub. No.: WO2014/054965
PCT Pub. Date: Apr. 10, 2014

(65) Prior Publication Data
US 2015/0250763 A1 Sep. 10, 2015

(30) Foreign Application Priority Data
Oct. 1, 2012 (RU) .................. 2012141642

(51) Int. Cl.
*A61K 31/13* (2006.01)
*A61K 31/4045* (2006.01)
*A61K 9/20* (2006.01)

(52) U.S. Cl.
CPC .......... *A61K 31/4045* (2013.01); *A61K 31/13* (2013.01); *A61K 9/20* (2013.01)

(58) Field of Classification Search
CPC ........................ A61K 31/13; A61K 31/4045
See application file for complete search history.

(56) References Cited

U.S. PATENT DOCUMENTS

2010/0081723 A1  4/2010  Jonas et al.

FOREIGN PATENT DOCUMENTS

| EP | 1 545 511 B1 | 6/2005 |
|----|--------------|--------|
| EP | 1 370 259 B1 | 1/2007 |
| RU | 2 445 973 C2 | 3/2012 |

OTHER PUBLICATIONS

International Search Report issued in corresponding International Application No. PCT/RU2012/000906 dated Jun. 14, 2003.

*Primary Examiner* — Zohreh A Fay
(74) *Attorney, Agent, or Firm* — Nath, Goldberg & Meyer; Tanya E. Harkins; Scott H. Blackman

(57) ABSTRACT

The invention relates to the field of pharmacology and practical medicine, namely, to the combined use of pharmaceutical compositions exhibiting a neurotropic action, alleviating manifestations of mental, behavioral, cognitive disorders in cases of organic damage of various origin to the central nervous system. The combination comprises Memantine and Melatonin in therapeutically efficient quantities. The combination enables to raise disease treatment effectiveness. 1 independent claim, 2 dependent claims. 2 examples, 7 tables.

3 Claims, No Drawings

COMBINATION FOR THE PROPHYLAXIS AND TREATMENT OF BEHAVIOURAL, MENTAL, AND COGNITIVE DISORDERS

FIELD OF THE INVENTION

The invention relates to the field of pharmacology and practical medicine, namely, to the combined use of pharmaceutical compositions exhibiting a neurotropic action, alleviating manifestations of mental, behavioral, cognitive disorders in cases of organic damage of various origin to the central nervous system.

PRIOR ART

It is known ["Endogenous-Organic Mental Diseases" by A. S. Tiganov (ed.)] that psychoorganic disorders appear, for example, at the background of slowly progressing, "no-stroke" clinical course, neurodegenerative diseases, a toxic damage to the brain, a metabolic damage to the brain, a damage to the brain due to the administration of psychoactive substances or due to any other exogenous symptomatic diseases of the CNS or in the result of acute disorders of cerebral circulation.

For example, the share of the psychoorganic syndrome of vascular origin, which does not reach the degree of dementia, accounts for 25% of the diagnosed cases of mental pathology in patients over 60 who turn to common polyclinics [N. M. Mikhailova, 1996]. Psychoorganic disorders may be diagnosed in such patients, manifesting events of torpidness, slow psychomotor reactions, light dysmnesic disorders, disorders of attention, and they are in close correspondence to the criteria of a "mild cognitive disorder" (ICD-10, entry F06.7 "Mild cognitive disorder").

It is said that an organic psychosyndrome is present in vascular brain diseases when observed changes in personality evidence more or less pronounced lowering of its level (loss of more refined and differentiated personal attitudes and behavioral forms, traits of disinhibition of lower attractions, etc.). Moreover, dysmnesic disorders, inaccuracies in orientation ("failure of internal clock"), low productivity of mental activities, critics and a level of judgments, depletion and impoverishment of notions, lowering of perception volume and clearness may be found. Hypertensic crises may be accompanied by individual psychotic manifestations, rudimentary hallucinoses that are regarded as transient mental disorders disappearing with lowering of an arterial pressure level.

Closeness, if not identity, of these conditions with not acutely manifested dementia symptoms in their initial stage of development follows from the list of disorders forming an organic psychosyndrome.

The pronounced problem of mental disorders of, in particular, vascular origin, is mainly pre-determined by its wide prevalence in patients over 45 who have essential hypertension and cerebral atherosclerosis in their history (M. S. Koushakovsky, 1995; Ye. Ye. Gogin, 1997; B. S. Vilensky, 1999; V. S. Volkov, Yu. M. Pozdnyakov, 1999; V. S. Myakotnykh et al., 1999; V. M. Kuzmenko, 2001; V. I. Skvortsova et al., 2006; N. M. Kaplan, E. Lieberman, 1994; A. H. Glassman, 1997; Hypertension control, 1997; G. Gross-Magnat, 2000; G. M. Martin, 2000; and others). This data proves a significant role of the above forms of pathology as a reason for mental disorders in this age. It is established that in this case signs of organic changes are present that, nevertheless, do not reach a degree of full-scaled dementia (S. I. Gavrilova et al., 1995; A. V. Medvedev, 1999; WHO Task Force, 1989; V. Hachinski, 1994; E. Murphy, G. Alexopoulos, 1995; and others). It is this totality that forms the notion of "psychoorganic syndrome" (E. Ya. Shternberg, 1983; A. S. Tiganov, 1983, 1999; B. N. Piven, 1996; V. V. Vandysh-Bubko, 2003; H. J. Gerts, S. Kanowski, 1983; B. Reisberg, 1986; N. Schmage et al., 1989; T. Yanagihara, 1991; C. Holmes, et al., 1999; A. J. Holland, 2000; K. A. Wesnes, J. E. Harrison, 2003; and others). At the same time, the typicalness of a combination of cognitive disorders with other psychopathic manifestations, mainly non-psychotic ones, is observed (B. A. Lebedev, 1988; N. M. Mikhailova, 1996; Yu. V. Popov, V. D. Vid, 1997; I. A. Chelysheva, 1997; N. M. Mikhailova, A. Yu. Kladova, 1999; B. N. Piven et al., 2006; S. I. Finkel, 1996; A. Kurz, 1998; C. G. Lyketsos et al., 1999; and others).

A psychoorganic syndrome, e.g., of vascular origin, is manifested, mainly, in elderly and old age (according to the WHO classification) (Ye. M. Melnik, 1990; A. U. Tibilova, 1991; and others), which determines the necessity of corresponding therapeutic approaches in the context of general principles of therapy of corresponding disorders. It is important to note in this connection that lowering of compensatory possibilities in elderly patients contributes to their hypersensitivity to psychological-traumatic and somatic-biological influences that may interfere with a treatment process and lower its effectiveness (A. U. Tibilova, 1990; A. U. Tibilova, Ye. M. Melnik, 1993; E. Finch, T. Kirkwood, 2000; and others). In an age over 45 such influences are observed rather frequently. They include: loss of relatives with formation of a loneliness situation, retirement, lowering of physical abilities, "accumulation" of chronic somatic diseases (N. F. Shakhmatov, 1996; V. N. Anisimov, M. V. Soloviev, 1999; V. N. Shabalin, 1999; K. Victor, 1987; S. J. Eisendrath, 1992; E. A. Murphy, 1994; R. Arking, 1998; and others). And several variants of somatic pathology not only exert direct biological influence on a mental condition, but also include a powerful psychological-traumatic factor, since they are considered by patients as a threat to their physical health and the life itself (V. I. Krylov et al., 1985; N. G. Neznanov, 1985; A. V. Gnezdilov, 2002; and others). Since there is a tendency to increasing the life period (so-called "live-out period"), improving medical care, increasing information burden and other situations, including stress ones, the relevance of the psychoorganic syndrome problem grows.

A separate problem is rational pharmacotherapy with due regard to the patient's age. In this connection, together with the significance of observing the general principles of drug therapy, treatment of patients of late ages with specialized substances for the purpose of correcting both age-related changes and cognitive functions has its significant peculiarities. And enlargement of the circle of new-generation preparations is to mainly resolve the problem of safe pharmacotherapy for these age groups.

A main clinical manifestation of the psychoorganic syndrome, alongside with disorders of memory, attention, asthenia, is the specific disorder of the "sleep-wakefulness" cycle, when the wakefulness level is low during a day and night sleep is impaired at night. Such rhythm disorder is a factor that independently impairs the patient's functioning and aggravating other symptoms of the disease. The clinical efficacy of Melatonin in respect of circadian rhythm normalization is known, namely, restoration of quality night sleep without undesired influence on the wakefulness level during a day ("Results and Prospects of Studying Physiological, Pathogenetic and Pharmacological Effects of Melatonin" (in Russian), N. N. Kaladze, Ye. M. Soboleva, N. N.

Skoromnaya, Crimea State Medical University Named After S. I. Georgiyevsky, Simferopol, 2 (23) 2010/Teoretichna Medicina).

It is observed during experiments with animals and therapy of elderly patients, both in normal condition and with various forms of cerebral pathology, including those of vascular origin, that Melatonin improves the processes of memory, visual and aural perception and concentrates attention. These facts determine medical capabilities of Melatonin as a potential nootropic agent [E. B. Aroushanyan, "Is Epiphysis Hormone Melatonin a New Nootropic Agent? (in Russian)//Exper. and clin. pharmacol.-2005.-V.68.-p. 74-79.; E. B. Aroushanyan "Epiphyseal Hormone Melatonin and Neurological Pathology" (in Russian)//Rus. Med. Journ.-2006.-V.14.-p. 1057-1063.].

Also, it is known that 1-aminoalkylcyclohexanes are capable of relieving mental and behavioral disorders during psychoorganic diseases, which leads to improving the patients' daily functioning. In particular, Memantine and other 1-aminoalkylcyclohexanes have proved their usefulness for lowering various progressive neurodegenerative disorders, such as dementia in patients with moderate and severe Alzheimer's disease, Parkinson's disease and muscular spasticity, as disclosed in U.S. Pat. Nos. 5,061,703; 5,614,560 and 6,034,134.

Melatonin (INN) is a neuropeptide that is synthesized by the epiphysis and exerts a unique influence on human and animal organisms. Melatonin (INN) helps to organize daily periodization and regulate cyclic processes, being a mediator between the pace-maker mechanism of suprachiasmatic nuclei (SCN) and the peripheral organs. The epiphysis, together with the hypothalamus SCN, is included into the so-called system of the body biological clock playing a key role in the mechanisms of "counting inner time" and ageing [E. B. Aroushanyan, 2005; V. N. Anisimov, 2007]. According to initial data, the main functions of the epiphysis in the body are: regulation of circadian and seasonal rhythms; regulation of the reproductive function; anti-oxidant protection and anti-tumor protection [V. N. Anisimov, 1998, 2003].

As to its chemical structure, Melatonin (INN) or N-acetyl-5-methoxytryptamine is a derivative of the biogenic amine Serotonin that, in its turn, is synthesized from the exogenous acid Tryptophan. It is known that Melatonin is formed in the epiphyseal cells and then is secreted into blood, primarily in the dark time of the day, at nights. Light, especially in the morning and daylight, sharply suppresses the production of this hormone. The epiphysis receives data on light load along a complex nerve pathway. The hypothalamus SCN plays the dispatcher role in this pathway. Information from the retina comes to SCN via a branch of the optic nerve, and then these signals come down through the hypothalamus via the pathways along the brainstem into the cervical spinal cord, from where the signals come back to the brain through holes of the scull and, at last, reach the epiphysis. At night and/or in the dark, when a significant part of the SCN neurons are at the dormant state, these nerve endings secrete noradrenaline activating the synthesis of enzymes, which are involved in the synthesis of Melatonin, in the epyphiseal cells—pinealocytes. The epiphysis of a healthy adult secretes approximately 30 μg of Melatonin during a night. Bright light blocks its synthesis instantly. In a case of constant dark, the daily rhythm of secretion, as supported by periodical activity of SCN, is maintained. Thus, a maximum content of Melatonin in the epiphysis and in the patient's blood falls on night hours, and a minimum one—in the morning and daylight. Though the epiphysis is the main source of Melatonin circulating in blood, as in the case of the other endocrine organs, the paracrine synthesis of Melatonin is also found practically in all the organs and tissues, such as: the thymus, the gastrointestinal tract, the gonads, connecting tissues [R. J. Reiter; I. M. Raikhlin, I. M. Kvetnoy; G. Huether]. Such a high level of duplication of Melatonin synthesis in the body only stresses its vital necessity for human life activity.

Apart from the circadian/rhythm-organizing effect, Melatonin has a number of other established properties, namely, a pronounced ant-oxidant and immunomodulatory actions. A number of authors suppose that the epiphysis controlling through Melatonin the endocrine, nervous and immune systems, integrates a systemic reaction to unfavorable factors by acting on the body resistance, though this statement is questionable, since Melatonin, in its turn, is subjected to higher regulation. Melatonin independently and directly links free oxygen radicals and, simultaneously, starts the natural system of anti-oxidant protection by activating SOD and catalase. As an anti-oxidant, Melatonin acts in a generalized way, since it is capable of passing through all biological barriers. Studies in vitro show that Melatonin exhibits far greater anti-oxidant activity for interrupting processes of lipid peroxidation and inactivation of active free radicals —OH and ROO—, as compared to known anti-oxidants [Reiter et al., 1995]. It is found that Melatonin plays a significant role in immunoregulation [I. M. Kvetnoy]. According to some studies, it is capable of exerting double influence on the functioning of the immune system. Thus, distinct stimulation is observed at the background of its preliminary depression, and the secondary administration of Melatonin in low doses to animals weakens the malproduction of antibodies and, at the same time, improves antivirus stability. In the situation of initial hyperactivity of the immune system, Melatonin, by the dose-dependent action, blocks formation of a number of cytokines in response to introduction of phytohemagglutinin and suppresses the functioning of activated macrophages and T-helpers.

It is supposed that the Melatonin immunocorrection is based on its direct action, through specific receptors, on the function of lymphoid organ cells and blood cell elements. There exists data evidencing its mediated effect through regulation of opioid mechanisms and modification of corticosteroid production by the adrenal cortex.

Melatonin exerts regulatory influence on the lipid and carbohydrate metabolism. It is capable of normalizing the process of lipid oxidation, thus reducing the possibility of atherosclerosis development, influences the endocrine control of arterial pressure (AP), reduces ACTH release and production of noradrenaline, vasopressin and renin [V. D. Slepushkin, 1990; G. V. Dolgov, 2004].

A Melatonin quantity changes during the whole life of a human being. The hormone secretion starts in the third month of child development, and its concentration reaches its maximum in the first years of life (not later than in 5 years). Until the sexual maturity period the Melatonin synthesis remains at a constant and high level, and after this its production falls sharply and continues reducing for 5 more years. Thereafter, the Melatonin production is not changed until the age of 40-45 years, and then its quantity begins lowering steadily, which concurs with the beginning of menopause, and this process continues until the end of the human life.

During recent decades facts have been accumulated, evidencing that Melatonin exhibits a totality of multiple effects which may be possibly evaluated as a positive influence on the biological functioning of a mammalian organism, and not only in the state of functional balance and health, but also during development and actual presence of pathological conditions.

A number of publications characterize Melatonin as a therapeutic agent used for correcting and/or stabilizing various pathological conditions. "Intravenous introduction of Melatonin reduces intracerebral inflammation arising due to transient focal cerebral ischemia in rats." [J Pineal Res. 2007 April; 42(3):297-309] They also demonstrate the Melatonin capability of blocking cell inflammation after cerebral ischemia and exerting a pluripotential action. "Pre-clinical assessments of Melatonin pharmacokinetics and safety in propylene glycol for intravenous introduction" [J Pineal Res. 2006 November; 41(4):337-43]. Melatonin in propylene glycol significantly raises Melatonin levels in plasma without serious toxic effects. "Melatonin reduces the serotonin release in the brain, arterial pressure and heartbeat rate in rats" [Pharmacology. 1993 August; 47(2):91-7.]. "Melatonin improves the cerebral circulation at maximum disorders in rats" [Am J Physiol. 1998 July; 275(1 Pt 2):H139-44.]. "Melatonin improves tonus of the pia mater of the brain and lowers the lower limit of the cerebral blood flow autoregulation" [Fundam Clin Pharmacol. 2001 August; 15(4):233-8.]. "Melatonin effects on arterioles in the pia mater of the brain in rats in natural conditions" [Br. J Pharmacol. 1999 August; 127(7):1666-70.]. "PET (Positron emission tomography) and plasma pharmacokinetic studies after bolus dosing of Melatonin in the human organism" [Int J Rad Appl Instrum B. 1991; 18(3):357-62.]. The results confirmed that Melatonin easily passed through the hematoencephalic barrier. "Delayed therapy with Melatonin improves electrophysiological restoration after transient focal cerebral ischemia in rats" [J Pineal Res. 2004 January; 36(1):33-42.]. "Melatonin alleviates damages to the gray and white substances in a mouse model at transient focal cerebral ischemia" [J Pineal Res. 2005 January; 38(1):42-52]. "Melatonin reduces neurovascular oxidative and nitrate-dependent (nitrosative) damages and protects against early permeability of the hematoencephalic bather after transient focal cerebral ischemia in mice" [J Pineal Res. 2006 September; 41(2):175-82]. "Melatonin reduces spread of neuron death after focal ischemia of medium degree in mice by inhibiting caspase-3 and is suitable as an additional therapy during treatment of a tissue-type plasminogen activator" [J Pineal Res. 2004 April; 36(3):171-6]. "Melatonin improves condition at neurological damages and neurophysiological deficit in experimental stroke models" [Ann N Y Acad Sci. 2003 May; 993:35-47; discussion 48-53.].

It may be prognosticated from the above-mentioned publications, which reflect various multiple articles on the therapeutic activity of Melatonin, that Melatonin exhibits a pronounced therapeutic activity. Being an endogenous substance present in a mammalian organism, Melatonin is a regulating agent with evolutionary acting mechanisms of its endogenous utilization. It means that its therapeutic breadth is within a very satisfactory range for clinical use.

The known and clinically used effects of Melatonin treat insomnia "Sleep Disorders and Principles of Their Correction" [L. A. Vakulenko//NMT.-2001-No. 6-p. 36-37.], "The use of melatonin for the treatment of insomnia" [Zisapel N.//Biol. Signals Recept.-1999.-V. 8, No. 1-2.-p. 84-89.]. Also, according to results of many studies, Melatonin has a positive regulatory effect during various stress conditions, "Effects of melatonin on vascular reactivity, catecholamine levels, and blood pressure in healthy men" [Arangino S. et al.//Am. J. Cardiol.,-1999.-V. 83, No. 9.-P. 1417-1419.

8. Avery D. Guidelines for prescribing melatonin//Ann Med.-1998.-V. 30, No. 1.-p. 122-130.], "Pineal gland buffers initial stress-induced ACTH burst" [Milin J., Demajo M., Milin R.//Acta boil. Iugosl.-1998.-V. 24, No. 2.-p. 171-176.], "The human pineal gland respond to stress-induced sympathetic activation in the second half of the dark phase: preliminary evidence" [Monteleone P., Maj M., Franza F. et al.//J. Neural Transmission-General Section.-1993.-V. 92, No. 1.-p. 25-32.], "A review of the evidence supporting melatonin's role as an antioxidant" [Reiter R. J. et al.//J. Pineal. Res.-1995.-V. 18, No. 1.-p. 1-11.]. This sleep-regulating property is also reflected in U.S. Pat. Nos. 4,600,723 and 5,242,941.

Melatonin also exhibits activity inhibiting ovulation (Chu et al. Endocrinology, 75, 238 (1964)) and activity in relation to MCF-7 human breast cancer cells (Blask et al., J. Neural, Transm./Supp/, 21, 433 (1986)) and is used for treatment of breast cancer in mammals (Black et al. Neuroendocrinol Lett, 9 (2) 63 (1987)). The neuroprotective activity of Melatonin is described that significantly manifests itself only when this preparation is administered at night. An important part of the neuroprotective activity mechanism is the capacity of this epiphysis hormone of alleviating oxidant-stress consequences and correcting cardiovascular disorders comorbid to an organic damage to the CNS (Pei Z., Pang S. F., Cheung T. F Administration of melatonin after onset of ischemia reduces the volume of cerebral infarction in a rat middle cerebral artery occlusion stroke model// Stroke-2003.-V.32-p. 770-775).

The Memantin effects are not associated with time of administering drugs due to circumstances secondary for the preparation medicinal effect; it is recommended that the preparation should be administered in the first half of the day—during daylight hours. Actually, the AM medicinal action mechanism is associated with alleviation of consequences of excitotoxicity being formed at an organic damage of the CNS.

Melatonin is sold under various trade names, both as a single composition and as in combination with vitamins. Trade names, such as "Melaxen", "Melatonex", "Night-Rest", "Sleeping Beauty", "Melatrol" are known, still more are offered under the name "Melatonin".

The following RF Patents are known: No. 2268737 "Method for treating atopic dermatitis" by administering Melatonin in dosage of 3 mg at 9 PM, the course is 21 days; No. 2428183 "Use of Melatonin as an adaptogen"; No. 2418586 "Method for correcting disorders in reproductive organs by administering melatonin"; No. 2394571 "Method of treating such inflammatory diseases of the intestine by administering Melatonin 40 minutes before sleep"; No. 2336890 "Compositions comprising Melatonin, *ginkgo biloba* and biotin" disclosing a composition for stimulating hair growth; No. 2294741 "Method for treating patients with ischemic heart disease" disclosing the use of Melatonin at the background of standard therapy; RU Application 2008150624 (PCT Application in US 373,06,2007 20070521) "Treatment of depressive disorders"; RU Application 2009141713 (PCT Application in US 100,06,2008 20080411) "Compositions for protection against ischemia/reperfusion" where Melatonin is mentioned in a combination; RU Application 2009137472 "Tablet of Melatonin and methods for making and using same" comprising Melatonin in dissolved state and associated with a pharmaceutically acceptable carrier; RU Application 97113435 "Method for treating drug addiction".

Memantin is a NMDA-antagonist that provides neuroprotective, antispastic, antiparkinsonian actions. It blocks glutamatergic neurotransmission and progression of neurodegenerative processes, exerts neuromodulating action, facilitates normalization of mental activities, improves memory, raises ability of concentrating attention and correcting locomotive disorders.

Various patents are known, e.g.: RU Patent No. 2336062 "Method for treating myopic astigmatism" wherein Memantin, as a neuroprotector, is administered 1 tablet daily for 2 weeks; RU Patent No. 2326660 "Oral medicinal preparation Memantin (variants) and method for producing same (variants)"; RU Application 2009124922 "Memantin pharmaceutical composition"; RU Application 2009103658 "Memantin pharmaceutical composition" comprising Memantine in granules; RU Application 2007140348 "Methods and compositions for treating CNS diseases"; RU Application 2007139712 "Composition comprising an anti-dementia agent"; EA012036 "Memantin for treating behavioral disorders in children's age"; EA011446 "Preparative forms of oral Memantin formulations with modified release"; EA013474 "Composition in the form of granules with Memantin modified and instant release"; etc.

In spite of multiple works confirming practicality of using the said preparations in the clinical practice of treating patients with CNS organic damage of various origin, attempts are made for developing more efficient agents and methods for treating patients with similar disorders due to a growth in a number of diseases accompanied by a whole complex of disorders. In particular, attempts have been made to provide preparation combinations.

The following patents are known: EA007632 "Combination of a NMDA-antagonist and inhibitors of acetylcholinesterase for treating Alzheimer's disease"; EA008863 "Combined therapy with the use of derivatives of 1-aminocyclohexane and inhibitors of acetylcholinesterase "; EA009668 "IFN-beta individually or in combination with other medicinal preparations for treating Alzheimer's disease and disorders related to dementia"; EA010430 "Combination of a NMDA-receptor antagonist and a selective inhibitor of serotonin recapture for treating depression and other mental disorders".

However, these combinations are efficient at particular CNS pathologies only.

SUMMARY OF THE INVENTION

The objective of this invention is to provide an efficient combined agent relieving manifestations of mental, behavioral, cognitive disorders in the event of an organic damage of various origin to the CNS.

This object is attained by a combination that ensures achievement of a synergetic therapeutic effect by simultaneously administering two therapeutic agents, namely, the Memantin preparation that is a modulator of the glutamatergic system and the Melatonin preparation that is the main hormone of the epiphysis—the regulator of diurnal rhythms.

The proposed combination comprises therapeutically efficient doses of Melatonin (INN) and Memantin (INN), which enables to ensure the technical effect of significantly higher therapeutic effect of joint use and improvement of the life quality. This helps to achieve the synergetic effect that enables not only achieve multiple effects simultaneously, but also improve their manifestation significantly, e.g., improve mental and physical workability and psychoemotional stability, correct sleep and wakefulness rhythm disorders in patients with CNS organic diseases of various origin.

The use of Melatonin together with Memantin in a combined application ensures a high compliance level necessary for achievement of such synergy. This also ensures exclusion of a number of side effects possible during monotherapy with these preparations, e.g., headache, hypertension.

Therapeutically efficient is the following contents of the components, in mg: Melatonin—in the range from 0.01 mg to 50 mg, and Memantin in the range from 0.01 to 100 mg. A preferable ratio is from 1:4 to 1:20.

The combination may be used from 1 to 5 times daily.

The combination may have the form of a tablet, including a sublingual form, a capsule, a formulation with modified release, a form for injection, a suppository, a powder for preparing a beverage, drops, including nasal drops, transdermal, transbuccal, aerosol forms.

Both components may be included into a single formulation or may be used as a kit comprising individual preparative forms.

DESCRIPTION OF THE BEST EMBODIMENT

Examples of the Formulations:
1. Tablet composition, in mg:
Memantin 100
Melatonin 5
Lactose 70
Microcrystalline cellulose 24.75
Starch 26
Povidone 12.5
Cross-carmellose 9.75
Calcium stearate 2
2. Drops composition, mg/mL
Memantin 10
Melatonin 0,5
Potassium sorbate 20
Mannit 5
Water—the rest.

Study of Pharmacological Activity

In order to confirm synergistic effects, several experiments were conducted with animal models.

For this, the active substances Melatonin 3 mg/Memantin 10 mg, Melatonin 5 mg/Memantin 20 mg, Melatonin 10 mg/Memantin 20 mg were taken, and doses recommended for human beings were converted into doses adapted for mice according to the formula "(active substance/70(average weight of a human being))×7". Then the compositions were dissolved in 5 mL of the solution and, according to the given formula, introduced to animals intraperitoneally once a day for 5 days.

The action of the compositions on learning and memory factors were studied on white non-linear male mice having a weight 20+/−4 g, using the conditioned passive avoidance reflex (CPAR) of electroconvulsive shock (ECS) (Ya. Buresh et al., 1991; K. M. Dyumaev et al., 1995).

Electroconvulsive shock (ECS) was used as the amnesic action, the electric current parameters were: 50 Hz, 50 mA, 0.3 s, which was applied to mice with the use of electrodes in the shape of clips fixed on auricles, transpineally, just after teaching CPAR (see, "Manual for Experimental (Pre-Clinical) Studies of New Pharmacological Substances", 2000). Pseudo-electroconvulsive shock was caused to the animals by applying pineal electrodes for causing ECS without applying electric current. The mice were tested for maintaining CPAR in certain time intervals after ECS.

The CPAR test is the main model for evaluating substance influences on formation and replication of short-time memory in a normal condition and in an abnormal condition, i.e., induced amnesia. The CPAR is the most informative method among the methods that are used today for evaluating efficiency of substances with influence on the CNS of mammals (see, "Manual for Experimental (Pre-Clinical) Studies of New Pharmacological Substances", 2000). The CPAR (conditioned passive avoidance reflex in a dark, light chamber) was taught to the mice on the basis of electrodermal response according to the method proposed by Cumin et al. (1982) with due regard to the recommendations given by Mondadori et al. (1990). The installation for mice, as produced by Lafayette Instrument Co., USA, was a black chamber with the electrode floor and a white plastic platform that was arranged on the floor in the center of the chamber. The mice, one by one, were put onto the plastic platform. The animals went/jumped down onto the electrode floor where they received an electric current shock, i.e., punishment. Electric current was supplied after the time when an animal stood on the floor with all its four legs. The natural response of the animals is to go back to the current-free or safe platform. After several minutes of teaching, 5 minutes on the average, mice developed CPAR and remained on the safe platform. Tests for memorizing CPAR were conducted in successive time intervals after amnesic action. In a case where an animal went/jumped down onto the platform within 1 minute, it was recorded as having retrograde amnesia of the passive avoidance skill. The compositions were studied in comparison with Melatonin 5 mg (mono-use) and Memantin 10 mg (mono-use), according to the above formula for adapting to animal models.

TABLE 1

| Therapeutic agent (dose) and ECS | Mice total number | Number of mice taught to CPAR (%) |
|---|---|---|
| NaCl isotonic solution (false ECS) | 10 | 8 (80) |
| NaCl isotonic solution (control) + ECS | 10 | 7 (70) |
| Melatonin 5 mg + ECS | 12 | 9 (75) |
| Memantin 10 mg + ECS | 11 | 8 (82) |
| Melatonin 3 mg/Memantin 10 mg + ECS | 12 | 11 (92) |
| Melatonin 5 mg/Memantin 20 mg + ECS | 10 | 9 (90) |
| Melatonin 10 mg/Memantin 20 mg + ECS | 11 | 10 (91) |

TABLE 2

Influence of the compositions under study on amnesia in mice, as caused by electroconvulsive shock (ECS)

Reproduction of CPAR

| Animal group | 1 day after teaching | | 3 days after teaching | | 7 days after teaching | | 10 days after teaching | |
|---|---|---|---|---|---|---|---|---|
| | Latent time of entering into the dark chamber, s | Number of mice not entered into the dark chamber, % | Latent time of entering into the dark chamber, s | Number of mice not entered into the dark chamber, % | Latent time of entering into the dark chamber, s | Number of mice not entered into the dark chamber, % | Latent time of entering into the dark chamber, s | Number of mice not entered into the dark chamber, % |
| NaCl isotonic solution (control) + false ECS) | 156.0 ± 24.0 | 90 | 151.1 ± 13.8 | 80 | 145.2 ± 15.5 | 70 | 136.7 ± 26.2 | 60 |
| NaCl isotonic solution (control) + ECS | 77.5 ± 21.3* | 20 | 79.5 ± 19.4 | 30 | 83.9 ± 26.7 | 40 | 87.5 ± 28.1** | 40 |
| Melatonin 5 mg + ECS | 108.3 ± 21.7 | 66.7 | 105.6 ± 17.4 | 58.3 | 103.3 ± 21.2 | 58.3 | 103.2 ± 20.6 | 33.3 |
| Memantin 10 mg + ECS | 104.6 ± 19.2 | 36.3 | 109.5 ± 22.1 | 54.5 | 110.1 ± 18.9 | 63.6 | 109.8 ± 21.1 | 63.6 |
| Melatonin 3 mg/Memantin 10 mg + ECS | 111.6 ± 16.3 | 83.3* | 112.4 ± 29.2* | 75 | 115.0 ± 19.8* | 66.7 | 113.2 ± 15.1* | 75* |
| Melatonin 5 mg/Memantin 20 mg + ECS | 116.1 ± 19.7* | 80* | 121.7 ± 21.3* | 70* | 123.0 ± 18.9* | 70* | 122.5 ± 19.8* | 60 |
| Melatonin 10 mg/Memantin 20 mg + ECS | 117.6 ± 19.7** | 81.8** | 120.6 ± 20.6** | 72.7** | 121.3 ± 21.8** | 63.6 | 120.9 ± 16.9** | 72.7** |

*Reliability of differences in comparison with Control group + false ECS of mice at $p < 0.05$ (Student's t-test; %).
**Reliability of differences in comparison with Control group + ECS at $p < 0.05$ (Student's t-test; %).

Thus, ECS caused retrograde amnesia of the passive avoidance skill in most of the mice, 80% of the animals ($p<0.001$) exhibited amnesia of learned skill in 24 hours. Melatonin and Memantin changed the amnestic action. The compositions comprising Memantin and Melatonin weakened the amnestic effect significantly ($p<0.05$). And the compositions under study were superior, as to the pronouncement of action, to Melatonin and Memantin separately.

Further, the anti-amnestic action of the compositions under study was studied on white non-linear male mice having a weight of 20-24 g on a model of amnesia caused by scopolamine, teaching CPAR to the animals according to the above-described method. The model of scopolamine amnesia was reproduced by intraperitoneally introducing m-cholinergic antagonist in the dose of 1 mg/kg just after teaching CPAR ("Manual for Experimental (Pre-Clinical) Studies of New Pharmacological Substances", 2000). The compositions under study were dissolved in 5 mL of the solution and, according to the above formula, introduced to the animals intraperitoneally, once a day for 5 days.

TABLE 3

| Therapeutic agent (dose) and ECS | Mice total number | Number of mice taught to CPAR (%) |
|---|---|---|
| NaCl isotonic solution (control) | 11 | 90.9 |
| Scopolamine (1 mg/kg) | 12 | 58.3 |
| Melatonin 5 mg + scopolamine | 11 | 66.7 |
| Memantin 10 mg + scopolamine | 10 | 70 |
| Melatonin 3 mg/Memantin 10 mg + scopolamine | 12 | 75 |
| Melatonin 5 mg/Memantin 20 mg + scopolamine | 11 | 72.7 |
| Melatonin 10 mg/Memantin 20 mg + scopolamine | 11 | 81.8 | container filled with water and equipped with a rotating wheel. After teaching CPAR, the mice swam in cold water, simultaneously rotating the wheel to the point of exhaustion. The CPAR maintenance was checked in successive time intervals. As false imitation of swimming in cold water, mice were put onto a pad consisting of wet cold wadding. The substances and an isotonic solution of sodium chloride (control) were studied in comparison with Melatonin 5 mg (mono-use) and Memantin 10 mg (mono-use), in accordance with the above formula for adapting to animal models, by intraperitoneal introduction before teaching mice, once a day for 5 days.

TABLE 4

Influence of the compositions under study on amnesia in mice, as caused by scopolamine

| | Reproduction of CPAR | | | | | | | |
|---|---|---|---|---|---|---|---|---|
| | 1 day after teaching | | 3 days after teaching | | 7 days after teaching | | 10 days after teaching | |
| Animal group | Latent time of entering into the dark chamber, s | Number of mice not entered into the dark chamber, % | Latent time of entering into the dark chamber, s | Number of mice not entered into the dark chamber, % | Latent time of entering into the dark chamber, s | Number of mice not entered into the dark chamber, % | Latent time of entering into the dark chamber, s | Number of mice not entered into the dark chamber, % |
| NaCl isotonic solution (control) | 161.2 ± 19.1 | 90.9 | 155.1 ± 17.6 | 72.7 | 151.2 ± 21.2 | 63.6 | 147.7 ± 18.5 | 54.5 |
| Scopolamine | 72.3 ± 25.6* | 25 | 76.1 ± 12.9 | 33.3 | 81.2 ± 21.4 | 41.6 | 84.7 ± 22.1 | 50 |
| Melatonin 5 mg + scopolamine | 111.3 ± 15.7 | 58.3 | 107.4 ± 21.2 | 54.5 | 105.8 ± 17.4 | 45.4 | 101.2 ± 20.6 | 36.3 |
| Memantin 10 mg + scopolamine | 110.8 ± 25.8 | 50 | 114.4 ± 18.2 | 60 | 111.1 ± 21.2 | 40 | 108.6 ± 18.7 | 40 |
| Melatonin 3 mg/Memantin 10 mg + scopolamine | 108.5 ± 12.5 | 66.6 | 110.4 ± 29.2 | 66.6 | 111.0 ± 14.5 | 75 | 114.7 ± 13.7* | 83.3 |
| Melatonin 5 mg/Memantin 20 mg + scopolamine | 110.1 ± 16.5 | 72.7* | 113.7 ± 17.4* | 81.8 | 115.0 ± 14.7 | 81.8 | 118.5 ± 24.5 | 63.6 |
| Melatonin 10 mg/Memantin 20 mg + scopolamine | 107.6 ± 24.4 | 63.6 | 109.5 ± 11.9 | 72.7 | 114.7 ± 27.6** | 81.8 | 112.9 ± 17.2 | 81.87 |

Scopolamine provoked retrograde amnesia of the skill in a significant number of the mice; CPAR amnesia was observed in 90% of the animals (p<0.001) in 24 hours. Individual application of Melatonin and Memantin influenced on amnesia of the skill obtained, but insignificantly.

The compositions comprising Melatonin+Memantin weakened the amnestic effect significantly, 1.5 times in a variable degree of variation. The compositions comprising Melatonin+Memantin were superior as to effects of mono-use of individual Melatonin and Memantin and prevented the CPAR amnesia from developing.

The antiamnestic action of the compositions on the amnesia model induced by swimming of mice in cold water with wheel rotation to the point of exhaustion. Studies were conducted on white non-linear male mice having a weight of 20-24 g with developing CPAR in the animals as in the previous studies. The animals were put, one by one, into a

TABLE 5

Influence of the compositions under study on the amnestic effect caused by mice swimming in cold water, simultaneously rotating wheel to the point of exhaustion

| Therapeutic agent (dose) and ECS | Mice total number | Number of mice taught to CPAR (%) |
|---|---|---|
| NaCl isotonic solution + imitation of swimming in cold water (control) | 10 | 9 |
| NaCl isotonic solution + mice swimming in cold water, simultaneously rotating wheel to the point of exhaustion | 11 | 90.9 |
| Melatonin 5 mg + mice swimming in cold water, simultaneously rotating wheel to the point of exhaustion | 13 | 84.6 |
| Memantin 10 mg + mice swimming in cold water, simultaneously rotating wheel to the point of exhaustion | 12 | 91.6 |

TABLE 5-continued

Influence of the compositions under study on the amnestic effect caused by mice swimming in cold water, simultaneously rotating wheel to the point of exhaustion

| Therapeutic agent (dose) and ECS | Mice total number | Number of mice taught to CPAR (%) |
|---|---|---|
| Melatonin 3 mg/Memantin 10 mg + mice swimming in cold water, simultaneously rotating wheel to the point of exhaustion | 13 | 84.6 |
| Melatonin 5 mg/Memantin 20 mg + mice swimming in cold water, simultaneously rotating wheel to the point of exhaustion | 13 | 76.9 |
| Melatonin 10 mg/Memantin 20 mg + mice swimming in cold water, simultaneously rotating wheel to the point of exhaustion | 11 | 90.9 |

TABLE 6

| Animal group | Reproduction of CPAR | | | | | | | |
|---|---|---|---|---|---|---|---|---|
| | 1 day after teaching | | 3 days after teaching | | 7 days after teaching | | 10 days after teaching | |
| | Latent time of entering into the dark chamber, s | Number of mice not entered into the dark chamber, % | Latent time of entering into the dark chamber, s | Number of mice not entered into the dark chamber, % | Latent time of entering into the dark chamber, s | Number of mice not entered into the dark chamber, % | Latent time of entering into the dark chamber, s | Number of mice not entered into the dark chamber, % |
| NaCl isotonic solution + imitation of swimming in cold water (control) | 152.2 ± 13.2 | 90 | 150.3 ± 14.4 | 70 | 147.2 ± 23.5 | 60 | 145.2 ± 18.5 | 60 |
| NaCl isotonic solution + mice swimming in cold water, simultaneously rotating wheel to the point of exhaustion | 69.4 ± 27.2 | 36.3 | 72.5 ± 12.9 | 45.4 | 74.1 ± 18.3 | 54.5 | 75.1 ± 12.7 | 54.5 |
| Melatonin 5 mg + mice swimming in cold water, simultaneously rotating wheel to the point of exhaustion | 109.3 ± 9.8 | 61.5 | 105.4 ± 13.5 | 46.1 | 104.6 ± 15.1 | 38.5 | 100.9 ± 17.4 | 30.7 |
| Memantin 10 mg + mice swimming in cold water, simultaneously rotating wheel to the point of exhaustion | 111.3 ± 22.3 | 41.6 | 115.9 ± 16.5 | 50 | 117.4 ± 28.1 | 66.6 | 118.0 ± 23.3 | 66.6 |
| Melatonin 3 mg/Memantin 10 mg + mice swimming in cold water, simultaneously rotating wheel to the point of exhaustion | 114.6 ± 23.7 | 69.2 | 117.5 ± 26.1 | 76.9 | 119.2 ± 24.2 | 84.6 | 120.3 ± 23.5 | 84.6 |
| Melatonin 5 mg/Memantin 20 mg + mice swimming in cold water, simultaneously rotating wheel to the point of exhaustion | 115.3 ± 18.2 | 76.9 | 118.4 ± 13.4 | 69.2 | 119.5 ± 17.8 | 76.9 | 117.4 ± 19.2 | 61.5 |

TABLE 6-continued

| | Reproduction of CPAR | | | | | | | |
|---|---|---|---|---|---|---|---|---|
| | 1 day after teaching | | 3 days after teaching | | 7 days after teaching | | 10 days after teaching | |
| Animal group | Latent time of entering into the dark chamber, s | Number of mice not entered into the dark chamber, % | Latent time of entering into the dark chamber, s | Number of mice not entered into the dark chamber, % | Latent time of entering into the dark chamber, s | Number of mice not entered into the dark chamber, % | Latent time of entering into the dark chamber, s | Number of mice not entered into the dark chamber, % |
| Melatonin 10 mg/Memantin 20 mg + mice swimming in cold water, simultaneously rotating wheel to the point of exhaustion | 116.1 ± 18.8 | 81.8 | 115.3 ± 16.2 | 72.7 | 117 ± 17.5 | 72.7 | 113.6 ± 14.1 | 61.5 |

Swimming in cold water also caused retrograde amnesia of the passive avoidance skill in most mice. The compositions also showed their effectiveness.

The antiamnestic action of the compositions was also carried out on an model of amnesia caused by acute normobaric hypoxic hypoxia with hypercapnia in a so-called hermetic chamber on white non-linear male mice having a weight of 20-24 Γ with the CPAR development in the animals according to the open-field method. After CPAR teaching the animals were put in the hermetic chamber for 16-18 minutes, depending on manifestation of hypoxia symptoms and weight. This model was reproduced by placing mice, one by one, in glass jars of equal volume that were hermetically sealed. With consumption of oxygen its concentration in the jar air and in the organism lowered and the quantity of carbon dioxide, on the contrary, raised. As the result, acute hypoxic hypoxia with hypercapnia developed in the animals. The animals of the control group were subjected to false hypoxia, that is, the mice were put in glass jars of equal volume that were not closed. The substances under study and the sodium chloride isotonic solution (control) were used in comparison with Melatonin 5 mg (mono-use) and Memantin 10 mg (mono-use) in accordance with the above formula for adapting to animal models by intraperitoneal introduction, before teaching the mice, once a day for 5 days.

TABLE 7

Influence of the compositions under study on CPAR in animals in the conditions of the open-field method after acute normobaric hypoxic hypoxia with hypercapnia

| Animal group | Horizontal motion activity | Vertical motion activity | Inspection of holes |
|---|---|---|---|
| | 1st day after operation | | |
| NaCl isotonic solution + false hypoxia (control) | 14.9 ± 5.2 | 6.2 ± 2.1 | 4.3 ± 1.3 |
| NaCl isotonic solution + hypoxia | 6.1 ± 3.1 | 3.0 ± 1.2 | 1.5 ± 0.9 |
| Melatonin 5 mg + hypoxia | 6.9 ± 2.3 | 3.2 ± 1.2 | 1.7 ± 0.6 |
| Memantin 10 mg + hypoxia | 7.1 ± 2.7 | 3.7 ± 1.9 | 2.1 ± 1.1 |
| Melatonin 3 mg/Memantin 10 mg + hypoxia | 8.5 ± 1.9 | 4.6 ± 3.1 | 1.3 ± 2.4 |
| Melatonin 5 mg/Memantin 20 mg + hypoxia | 8.7 ± 2.1 | 4.3 ± 2.8 | 2.3 ± 2.4 |
| Melatonin 10 mg/Memantin 20 mg + hypoxia | 8.4 ± 1.5 | 4.2 ± 2.7 | 2.0 ± 1.6 |
| | 3rd day after operation | | |
| NaCl isotonic solution + false hypoxia (control) | 14.1 ± 1.6 | 5.7 ± 2.1 | 2.8 ± 1.2 |
| NaCl isotonic solution + hypoxia | 5.9 ± 1.8 | 3.1 ± 1.2 | 1.3 ± 1.0 |
| Melatonin 5 mg + hypoxia | 8.2 ± 1.4* | 3.5 ± 0.9 | 1.9 ± 0.8 |
| Memantin 10 mg + hypoxia | 8.9 ± 4.9 | 3.3 ± 1.2 | 2.5 ± 1.1 |
| Melatonin 3 mg/Memantin 10 mg + hypoxia | 11.7 ± 3.1 | 4.2 ± 1.7 | 2.5 ± 0.9 |
| Melatonin 5 mg/Memantin 20 mg + hypoxia | 12.1 ± 2.5 | 4.4 ± 1.5 | 2.9 ± 1.3 |
| Melatonin 10 mg/Memantin 20 mg + hypoxia | 11.9 ± 3.2 | 4.5 ± 2.1 | 2.1 ± 1.4 |
| | 7th day after operation | | |
| NaCl isotonic solution + false hypoxia (control) | 13.5 ± 1.9 | 5.1 ± 2.1 | 3.4 ± 2.5 |
| NaCl isotonic solution + hypoxia | 7.0 ± 1.6 | 2.9 ± 2.4 | 1.9 ± 1.3 |
| Melatonin 5 mg + hypoxia | 8.3 ± 2.8 | 3.2 ± 1.3 | 2.4 ± 0.5 |
| Memantin 10 mg + hypoxia | 9.6 ± 3.4 | 3.7 ± 1.8 | 3.0 ± 2.7 |
| Melatonin 3 mg/Memantin 10 mg + hypoxia | 14.2 ± 2.6** | 5.1 ± 3.1 | 3.2 ± 1.4 |
| Melatonin 5 mg/Memantin 20 mg + hypoxia | 16.1 ± 1.6** | 5.3 ± 2.2 | 3.8 ± 1.7** |
| Melatonin 10 mg/Memantin 20 mg + hypoxia | 14.7 ± 2.6 | 5.3 ± 3.5 | 2.7 ± 2.4 |
| | 10th day after operation | | |
| NaCl isotonic solution + false hypoxia (control) | 13.8 ± 1.2 | 5.6 ± 1.3 | 3.5 ± 1.2 |
| NaCl isotonic solution + hypoxia | 6.3 ± 1.5 | 3.4 ± 2.7 | 2.0 ± 1.8 |
| Melatonin 5 mg + hypoxia | 8.1 ± 1.7 | 3.6 ± 2.3 | 2.6 ± 2.9 |
| Memantin 10 mg + hypoxia | 11.3 ± 1.7* | 4.1 ± 2.5 | 3.2 ± 1.3* |
| Melatonin 3 mg/Memantin 10 mg + hypoxia | 18.8 ± 1.9** | 5.9 ± 2.7 | 4.0 ± 2.6** |
| Melatonin 5 mg/Memantin 20 mg + hypoxia | 20.1 ± 3.1** | 5.9 ± 2.9 | 4.2 ± 1.1** |
| Melatonin 10 mg/Memantin 20 mg + hypoxia | 17.6 ± 3.2* | 3.7 ± 1.4 | 3.2 ± 1.3 |

*Reliability of differences in comparison with the animal group with false hypoxia at p < 0.05 (Student's t-test).
**Reliability of differences in comparison with hypoxia at p < 0.05 (Student's t-test)

Thus, the new combination exhibits high effectiveness in alleviating manifestations of mental, behavioral, cognitive disorders in cases of CNS organic damage of various origin.

Both preparations are capable of lowering intensity of nerve tissue damage by various unfavorable factors through different pathogenetic mechanisms. The simultaneously forming pharmacodynamic activity of both medicinal agents supplements significantly the action mechanism of each other, thus creating conditions favorable for an optimal realization of the therapeutic action potential in a case of CNS organic damage.

The combination may be indicated in cases of the following medical conditions that are accompanied by clinical manifestations of organic psychosyndrome (and its most significant component—dementia): Alzheimer's disease, vascular (multi-infarct) dementia, alcoholism, intracranial volume processes—tumors, subdural hematomas and cerebral abscesses, anoxia, craniocerebral trauma, normotensive hydrocephaly, Parkinson's disease, Huntington's chorea, progressive supranuclear paralysis, Pick disease, amyotrophic lateral sclerosis, spinocerebellar degenerations, ophthalmoplegia in combination with metachromatic leukodystrophy (adult form), Hallervorden-Spatz syndrome, hashish psychosis, late stages, infections, Creutzfeldt-Jakob disease, viral encephalitis, progressive multifocal leukoencephalopathy, neurosyphilis, Behçet's disease, chronic bacterial and fungal meningitis; deficiency conditions, Gayet-Wernicke-Korsakoff syndrome—thiamine deficiency, Vitamin B12 deficiency, folic acid deficiency, Vitamin B3 deficiency, pellagra; metabolic disorders, dialysis dementia, hypo- and hyperfunction of thyroid gland, severe renal insufficiency, Cushing's syndrome, hepatic failure, diseases of parathyroid glands, systemic lupus erythematosus and other collagen diseases accompanied by cerebral vasculitis, disseminated sclerosis, Whipple's disease.

What is claimed is:

1. A combination for treatment and/or prophylaxis of manifestations of vascular dementia, characterized in that it comprises Melatonin in an amount from 3 mg to 10 mg and Memantin in an amount from 10 to 20 mg.

2. The combination according to claim 1, characterized in that it is intended for introducing to a mammal, including a human being.

3. The combination according to claim 1, characterized in that it has the form of a tablet, including a sublingual form, a capsule, a formulation with modified release, a form for injection, a suppository, a powder for preparing a beverage, drops, including nasal drops, transdermal, transbuccal, aerosol forms.

* * * * *